United States Patent [19]

Umezawa et al.

[11] Patent Number: 4,525,299
[45] Date of Patent: Jun. 25, 1985

[54] (−)-15-DEOXYSPERGUALIN, PROCESS FOR THE PREPARATION THEREOF, AND INTERMEDIATE OF THE SAME

[75] Inventors: Hamao Umezawa; Tomio Takeuchi, both of Tokyo; Shinichi Kondo, Yokohama, all of Japan

[73] Assignee: Zaidan Hojin Biseibutsu Kagaku Kenkyu Kai, Japan

[21] Appl. No.: 493,209

[22] Filed: May 10, 1983

[51] Int. Cl.³ ............................................. C07C 103/52
[52] U.S. Cl. ............................................. 260/112.5 R
[58] Field of Search ................................. 260/112.5 R

[56]  References Cited

PUBLICATIONS

Umezawa, J. Antibiot., 34 (12), 1622-24, (1981).
Kondo, J. Antibiot., 34 (12), 1625-27, (1981).
Takeuchi, J. Antibiot., 34 (12), 1619-21, (1981).
Umezawa et al., J. Antibiot., 34 (12), 1622-4, (1980).

Primary Examiner—Delbert R. Phillips
Assistant Examiner—F. T. Moezie
Attorney, Agent, or Firm—Henry C. Nields

[57]  ABSTRACT (−)-15-Deoxyspergualin represented by the following formula

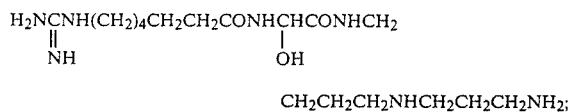

$CH_2CH_2CH_2NHCH_2CH_2CH_2NH_2$;

a salt thereof having antitumor activity, process for the preparation thereof and intermediate thereof.

4 Claims, No Drawings

(−)-15-DEOXYSPERGUALIN, PROCESS FOR THE PREPARATION THEREOF, AND INTERMEDIATE OF THE SAME

SUMMARY OF THE INVENTION

This invention relates to (−)-15-deoxyspergualin represented by the following formula [I]

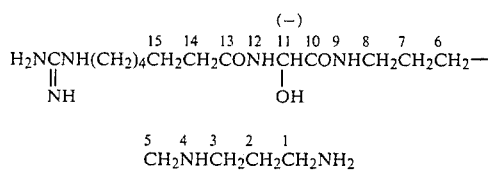

and its salts, a process for the preparation of these compounds, and to intermediates of these compounds.

BACKGROUND OF THE INVENTION

The inventors have discovered, during the course of their histological studies on antitumor agents, the novel antitumor antibiotic BMG 162-aF2, later named spergualin, in a broth for culture of *Bacillus laterosporus* BMG 162-aF2 (Deposit No. 5230 at the Fermentation Research Institute, Agency of Industrial Science and Technology, Ministry of International Trade and Industry of Japan), a strain belonging to the genus Bacillus (Journal of Antibiotics, Vol. 34, 1619–1622, 1981), The chemical structure of spergualin is represented by the following formula

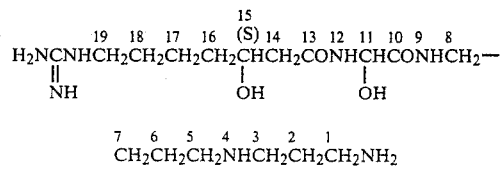

in which the configuration at the 15-position is S-configuration (sinister), but that at the 11-position has not been determined (Journal of Antibiotics, vol. 34, 1622, 1981).

The compound of this structural formula could also be synthesized by the condensation of an acid amide and glyoxylylspermidine, and the resulting epimer was divided into (−)-spergualin that naturally occurs and (+)-spergualin that does not (Journal of Antibiotics, Vol. 34, 1625, 1981).

DETAILED DESCRIPTION OF THE INVENTION

The inventors have now found that the optically active compound (−)-15-deoxyspergualin of the aforementioned general formula [I] produced by deoxygenation of (−) spergualin has a markedly superior carcinostatic action to 15-deoxyspergualin, a compound synthesized previously by the inventors through the condensation of (S)-7-guanidino-3-hydroxyheptanamide and N-[4-(3-aminopropyl)aminobutyl]-2,2-dihydroxyethanamide. This finding has led the inventors to complete this invention.

Since (−)-15-deoxyspergualin according to this invention is unstable in the form of free base, it should preferably be converted into a non-toxic salt through an addition reaction with a pharmacologically acceptable acid by a customary method.

Example of the acid-addition salt include salts with inorganic acids such as hydrochloric acid, sulfuric acid, phosphoric acid and boric acid, and salts with organic acids such as acetic acid, citric acid, tartaric acid and glutaric acid.

The physical and chemical properties and biological properties of (−)-15-deoxyspergualin of the general formula [I] in accordance with this invention are revealed below.

(1) Physical and chemical properties of (−)-15-deoxyspergualin trihydrochloride dihydrate The compound is colorless and syrupy, and its melting point can not be measured clearly. It shows $[\alpha]_D^{25} -7.3°$ (c: 1, water).

Its elementary analysis reveals C: 38.45%, H: 8.08%, N: 18.61%, Cl: 20.26%, which corresponds with the theory for $C_{17}H_{37}N_7O_3 \cdot 3HCL \cdot 2H_2O$ (C: 38.31%, H: 8.32%, N: 18.40%, Cl: 19.96%.

Thin-layer chromatography over slica gel using a butanol:pyridine:acetic acid:water (6:4:2:4 in volume ratio) mixture as a developer revealed a single spot (ninhydrin color reaction) at an Rf value of 0.17 (spergualin has an Rf value of 0.13). The antibacterial activity against *Bacillus subtilis* PCI-219 was 134% of that of (−)-spergualin (3HCL.½H$_2$O).I (2) Biological properties of (−)-15-deoxyspergualin trihydrochloride dihydrate Mouse Leukemia L1210 cells ($10^5$) were inoculated intraperitoneally to groups of 8 mice each. The test compound dissolved in physiological saline solution was intraperitoneally administered once daily for 9 consecutive days, starting on the day of inoculation. The animals were raised and observed for 60 days to determine survival rates (%). The survival rates were calculated from the following equation:

$$\frac{T \text{ [average period (in days of survival for the treated group]}}{C \text{ [average period (in days) of survival for the non-treated group]}} \times 100$$

The average survival period for the control (non-treatment) group was 7.6 to 8.9 days.

The test results are shown in Table 1 along with those obtained on (−)-spergualin.

TABLE 1

Efficacy of (−)-15-deoxyspergualin in the treatment of mouse Leukemia L1210

| Dose (mg/kg/day) | (−)-15-Deoxyspergualin* | | (−)-Spergualin** | |
|---|---|---|---|---|
| | T/C (%) | No. of mice survived for 60 days | T/C (%) | No. of mice survived for 60 days |
| 50 | | | 295 | 0/8 |
| 25 | | | 334 | 0/8 |
| 12.5 | | | >586 | 4/8 |
| 6.25 | 408 | 0/8 | >732 | 8/8 |
| 3.13 | >526 | 2/8 | >441 | 3/8 |
| 1.56 | >493 | 2/8 | >301 | 1/8 |
| 0.78 | >789 | 8/8 | 107 | 0/8 |
| 0.39 | >629 | 6/8 | | |
| 0.20 | >664 | 6/8 | | |
| 0.10 | 138 | 0/8 | | |
| 0.05 | 129 | 0/8 | | |

Notes:
*Trihydrochloride dihydrate
**Trihydrochloride hemihydrate (−)-15-Deoxyspergualin according to this invention is synthesized in the way mentioned below.

The hydroxyl group at the 15-position of a derivative of (−)-spergualin represented by the following general formula [II]

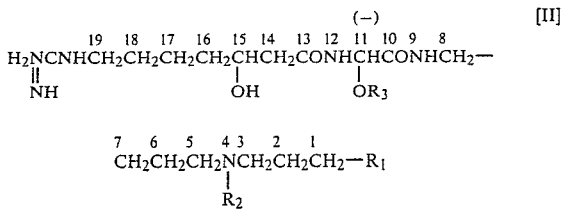

(wherein $R_1$ represents a masked amino group, and $R_2$ and $R_3$ each represent a masking group) is deoxygenated and then, the masking groups are eliminated to give the desired claimed (−)-15-deoxy- spergualin of the following formula [I]

or its acid-addition salts.

The amino group at the 1-position and the amino group at the 4-position in (−)-spergualin derivatives of the general formula [II] may be masked with amino-masking groups widely used in the synthesis of peptides. Since the compound of the formula [I] to be produced in this invention is very unstable to alkalis and acids, however, the masking should preferably be done using aralkyloxy-carbonyl groups, such as a phenylalkyl(-$C_1$–$C_4$)oxycarbonyl group which may be substituted by alkyl($C_1$–$C_4$)oxy group on the phenyl ring, for example, benzloxycarbonyl group and a p-methoxybenzyloxycarbonyl group, which can be easily eliminated by hydrogenolysis according to conventional manners. To introduce these amino-masking groups in (−)-spergualin, it is advantageous to use known methods, such as the active ester method. Generally, by these methods, these amino-masking groups do not react with the guanidine group of (−)-spergualin. The masking group for the hydroxyl group at the 11-position may be any group which can be introduced without isomerizing the compound, but it should preferably be a tetrahydropyranyl group. In order to attach a tetrahydropyranyl group selectively to the hydroxyl group at the 11-position without isomerizing the compound, 1 to 3 equivalents of 2,3-dihydro-4H-pyran is reacted with the compound in an anhydrous organic solvent, preferably, anhydrous N,N-dimethylformamide for 2 to 10 hours at room temperature in the presence of 0.1 to 3 equivalents, preferably, 0.2 to 1 equivalent, of an acid catalyst such as p-toluenesulfonic acid.

Preferably, the reaction with 2 equivalents of 2,3-dihydro-4H-pyran is performed for 7 hours in the presence of 0.5 equivalent of P-toluenesulfonic acid, whereby a tetrahydropyranyl group can be attached selectively to the hydroxyl group at the 11-position without isomerizing the compound. The resulting compound can be represented by the following general formula [III]

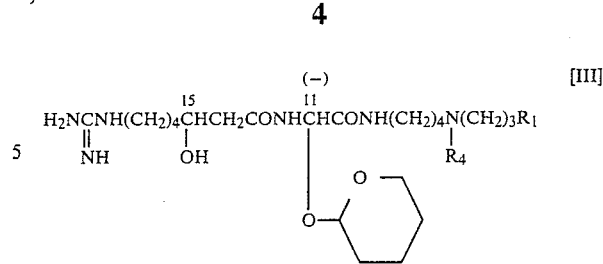

in which $R_1$ and $R_2$ are the same as defined previously. The configuration at the 11-position of (−)-1-N,4-bis-(benzyloxycarbonyl)-11-O-tetrahydropyranyl-spergualin so obtained has been confirmed to undergo no isomerization in view of the fact that (−)-spergualin with high optical purity was recovered after removing the amino-masking groups through hydrogenolysis with a weak acid to be mentioned later. The tetrahydropyranyl group is a mixture of the α and β anomers. Deoxygenation of the hydroxyl group at the 15-position of the (−)-spergualin derivative of the general formula [II] can be performed in a customary manner. For example, a method may be employed which comprises esterifying the hydroxyl group at the 15-position with sulfonic acid, then iodinating or brominating the compound, and dehalogenating it through catalytic reduction. More concretely, the (−)-spergualin derivative of the general formula [II] is treated firstly with a widely used sulfonyl compound, e.g., an alkylsulfonyl compound such as methanesulfonyl chloride, an arylsulfonyl compound such as p-toluenesulfonyl chloride, or an arylalkylsulfonyl compound such as benzylsulfonyl chloride, in a solvent such as anhydrous pyridine to thereby convert the hydroxyl group at the 15-position into a sulfonic acid ester.

Then, the resulting compound is reacted with a halogenating agent such as an alkali metal iodide or alkali metal bromide (e.g. sodium iodide or sodium bromide) in a solvent such as anhydrous N,N-dimethylformamide to obtain its derivative iodinated or brominated at the 15-position. Subsequently, the derivative is catalytically reduced in a solvent such as methanol, dioxane and water or their mixture by a customary method with the use of a catalyst such as palladium or platinum to cause dehalogenation, thereby achieving deoxygenation at the 15-position. If, in this case, the amino-masking groups are aralkyloxycarbonyl groups, the catalytic reduction also detaches these groups. The 11-O-tetrahyrdopyranyl group is easily eliminated by adding about 0.1 equivalent of p-toluenesulfonic acid to an aqueous solution of 2 equivalents of an acid-addition salt of this compound, and stirring the mixture while cooling it with ice. The reaction proceeds sufficiently within 5 to 7 hours. Purification of (−)15-deoxyspergualin obtained in this invention should preferably be performed by column chromatography over a cation exchange resin using a carboxyl group as the active group. It is recommended, for example, to absorb the compound to a column packed with CM-SEPHADEX ® C-25 (a product of Pharmacia, Sweden) equilibrated with 0.4 mol sodium chloride, and subject the absorbate to gradient elution involving 0.4 mol to 1.0 mol sodium chloride. The eluate is concentrated to dryness, and extracted with anhydrous methanol. The extract is applied to a column with a molecular sieve such as SEPHADEX ® LH-20 (a product of Pharmacia, Sweden), and then eluted with aqueous methanol for desalting. The eluate is concentrated to dryness to obtain the desired trihydrochloride of (−)-15-deoxyspergualin. Any desired addition salt is obtained depending on the type of a salt used in gradient elution from the CM-SEPHADEX ® column. This invention will be described in greater detail by reference to the following examples.

EXAMPLE 1

Synthesis of (−)-15-deoxyspergualin (a) (−)-1-N,4-bis(benzyloxycarbonyl)spergualin:

3.0 g (5.85 mmol) of (−)-15-spergualin trihydrochloride was dissolved in 30 ml of methanol, and 7.2 ml (17.6 mmol) of triethylamine was added to the solution. To the mixture was added a solution of 3.21 g (12.9 mmol) of N-benzyloxycarbonyloxysuccinimide in 8 ml of dioxane. The resulting mixture was stirred for 3 hours at room temperature. The reaction mixture was concentrated to dryness, and the resulting concentrate was dissolved in 50 ml of 0.1 mol sodium chloride.

The solution was adjusted to a pH of 6.5 with 2N hydrochloric acid, and applied to a column of CM SEPHADEX ® C-25 (200 ml) equilibrated with 0.1 mol sodium chloride. Then, gradient elution using 0.1 mol and 0.5 mol sodium chloride (1 liter each) was performed, to collect fractions of 20 ml each. Fraction Nos. 34 to 80 were put together, concentrated to dryness, and the concentrate was extracted 3 times with 10 ml of methanol. The extract was applied to a column of SEPHADEX ® LH-20 (200 ml), and eluted with 90% methanol for desalting, to collect fractions of 2 ml each. Fraction Nos. 51 to 63 were put together, concentrated and dried to obtain 3.8 g of (−)-1-N,4-bis(benzyloxycarbonyl)spergualin hydrochloride as a colorless syrupy mass.

Yield: 91% $[\alpha]_D^{21} -11°$ (c: 1, water). Found on elementary analysis: C: 54.95%, H: 7.25%, N: 13.83%, Cl: 5.06%. Theory for $C_{33}H_{49}N_7O_8 \cdot HCl \cdot \frac{1}{2}H_2O$: C: 55.26%, H: 7.17%, N: 13.67%, Cl: 4.94%.

(b) (−)-1-N,4-bis(benzyloxycarbonyl)-11-O-tetrahydropyranylspergualin:

3.45 g (4.81 mmol) of the (−)-1-N,4-bis(benzyloxycarbonyl)spergualin hydrochloride obtained in the above step (a) was dissolved in 30 ml of anhydrous N,N-dimethylformamide. To the solution were added 0.63 ml (9.75 mmol) of 2,3-dihydro-4H-pyran and 464 mg (2.44 mmol) of p-toluenesulfonic acid hydrate, and the mixture was stirred for 7 hours at room temperature. After the reaction, 0.33 ml (2.44 mmol) of triethylamine was added, and the mixture was concentracted to dryness. The resulting concentrate was purified by column chromatography using a column of silica gel (WAKO GEL ® C-200, 300 g) and a chloroform:methanol:pyridine: 50% acetic acid (240:40:4:1) mixture as a developer. Each fraction was collected in an amount of 20 ml. Fraction Nos. 66 to 78 were combined, concentrated to dryness to obtain 1.07 g of (−)-1-N,4-bis-(benzyloxycarbonyl)-11-O-tetrahydropyranylspergualin acetate as a colorless syrupy mass.

Yield: 26%. $[\alpha]_D^{22} -13°$ (C: 1, methanol). Elementary analysis values found: C: 56.65%, H: 7.76%, N: 11.75%. Theoretical values for $C_{38}H_{57}N_7O_9 \cdot CH_3COOH \cdot 3/2 H_2O$: C: 56.99%, H: 7.65%, N: 11.63%. Further, Fraction Nos. 85 to 92 were combined, concentrated to dryness to recover (−)-1-N,4-bis(benzyloxycarbonyl) spergualin acetate in an amount of 362 mg (yield: 10%).

(c) (−)-1-N,4-bis(benzyloxycarbonyl)-15-O-methanesulfonyl-11-O-tetrahydropyranylspergualin:

950 mg (1.13 mmol) of the (−)-1-N,4-bis(benzyloxycarbonyl)-11-O-tetrahydropyranylspergualin acetate obtained in the above step (b) was dissolved in 10 ml of anhydrous pyridine. To which 0.13 ml (1.74 mmol) of methanesulfonyl chloride was added while cooling with ice, and the mixture was stirred for 3 hours. After the reaction, 0.2 ml of water was added, and the mixture was concentrated to dryness. The concentrate was purified by column chromatography over silica gel (WAKO GEL ® C-200, 100 g) developed with a chloroform:methanol:pyridine: 50% acetic acid (320:40:4:1) mixture. The amount of each fraction was 20 ml. Fraction Nos. 16 to 25 were combined, concentrated to dryness to obtain 598 mg of an acetate of the title compound as a colorless syrupy material. The yield was 54%.

(d) (−)-1-N,4-bis(benzyloxycarbonyl)-15-deoxy-15-iodo-11-O-tetrahydropyranylspergualin:

591 mg (0.699 mmol) of the (−)-1-N,4-bis(benzyloxycarbonyl)-15-O-methanesulfonyl-11-O-tetrahydropyranylspergualin acetate obtained in step (c) was dissolved in 20 ml of anhydrous N,N-dimethylformamide. To this solution 5.02 g (33.5 mmol) of sodium iodide was added, followed by stirring the mixture for 15 hours at 90° C. The reaction mixture was concentrated to dryness, and the concentrate was dissolved in 30 ml of ethyl acetate. The solution was washed with 30 ml of a 20% aqueous solution of sodium thiosulfate and 30 ml of a saturated aqueous solution of sodium chloride. The ethyl acetate layer was dehydrated with anhydrous sodium sulfate, and concentrated to dryness. The concentrate was purified by a column chromatograph packed with silica gel (WAKO GEL ® C-200, 50 g) and developed with a 320:40:4:1 mixture of chloroform, methanol, pyridine and 50% acetic acid. The amount of each fraction collected was 10 ml. Fraction Nos. 7 to 28 were combined, concentrated to dryness to obtain 204 mg of an acetate of the title compound as a colorless syrupy material. The yield was 33%.

(e) (−)-15-deoxy-11-O-tetrahydropyranylspergualin:

198 mg (0.214 mmol) of the (−)-1-N,4-bis(benzyloxycarbonyl)-15-deoxy-15-iodo-11-O-tetrahydropyranylspergualin acetate obtained in the step (d) was dissolved in 20 ml of an 80% aqueous solution of methanol, to which 40 mg of a catalyst consisting of 5% palladium and barium carbonate was added, and the mixture was stirred in a hydrogen stream for 10 hours at room temperature. The catalyst was removed by filtration, and the filtrate was concentrated to dryness. The resulting concentrate was dissolved in 30 ml of a solution of 0.1 mol sodium chloride, and the solution was adjusted to a pH of 6.5 with 1N hydrochloric acid. Then, the solution was applied to a column of CM-SEPHADEX ® C-25 (a product of Pharmacia, Sweden, 40 ml) equilibrated with 0.1 mol sodium chloride.

Further, is was subjected to gradient elution involving 0.1 mol and 0.8 mol sodium chloride (200 ml each) to collect fractions in an amount of 4 ml each. Fraction Nos. 67 to 77 were combined, concentrated to dryness, and extracted 3 time with 5 ml of methanol. The extract was applied to as column of SEPHADEX® LH-20 (100 ml), and eluted with 90% methanol for desalting. The amount of each fraction was 1 ml. Fraction Nos. 36 to 47 were put together, concentrated to dryness to obtain 62.9 mg of a trihydrochloride of the title compound as a colorless syrupy material. The yield was 54%.

(f) (−)-15-deoxyspergualin:

61 mg (0.112 mmol) of the 15-deoxy-11-O-tetrahydropyranylspergualin trihydrochloride obtained in the step (e) was dissolved in 3 ml of water. The solution was cooled with ice, incorporated with 2.1 mg (0.011 mmol) of p-toluenesulfonic acid (H2O) and the mixture was stirred for 7 hours. After the reaction, the mixture was adjusted to a pH of 6.5 with 1M aqueous ammonia, and 10 ml of 0.4 mol sodium chloride was added. The mixture was applied to a column of CM-SEPHADEX® C-25 (20 ml) equilibrated with 0.4 mol sodium chloride, and subjected to gradient elution involving 0.4 mol and 1.0 mol sodium chloride (100 ml each). The amount of each fraction collected was 2 ml. Fraction Nos. 73 to 81 were combined, concentrated to dryness, and extracted 3 times with 5 ml of methanol. The extract was applied to a column of SEPHADEX® LH-20 (100 ml), and eluted with 90% methanol for desalting. The amount of each fraction was 1 ml. Fraction Nos. 38 to 48 were combined, concentrated to dryness to obtain 46.6 mg of (−)-15-deoxyspergualin trihydrochloride dihydrate as a colorless syrupy material. The yield was 78%.

We claim:

1. (−)-15-Deoxyspergualin represented by the following formula

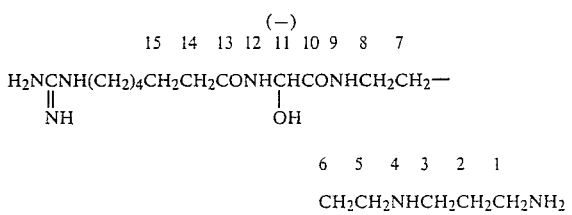

and its non-toxic salts.

2. A process for preparing (−)-15-deoxyspergualin of the formula

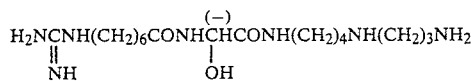

and its non-toxic salts which comprises the deoxygenation of the hydroxyl group at the 15-position of a derivative of (−)spergualin represented by the following general formula:

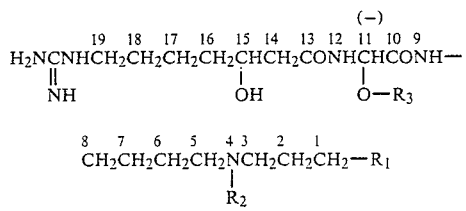

(wherein $R_1$ represents a phenylalkyl ($C_1$–$C_4$) oxycarbonylamino which may be substituted by alkyl ($C_1$–$C_4$) oxy group on the phenyl ring and $R_2$ represents a phenylalkyl ($C_1$–$C_4$) oxycarbonyl group which may be substituted by alkyl ($C_1$–$C_4$) oxy group and $R_3$ represents tetrahydropyranyl group) and then eliminating the masking groups.

3. A compound of the following general formula:

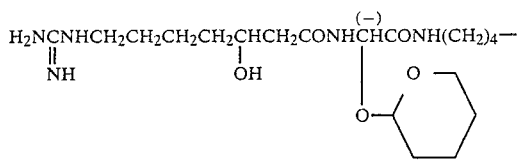

wherein $R_1$ represents a phenylalkyl ($C_1$–$C_4$) oxycarbonylamino which may be substituted by alkyl ($C_1$–$C_4$) oxy group on the phenyl ring and $R_2$ represents a phenylalkyl ($C_1$–$C_4$) oxy group and its non-toxic salts.

4. (−)-1-N,4-bis(benzyloxycarbonyl)-11-O-tetrahydropyranylspergualin and its non-toxic salts.

* * * * *